United States Patent
Kim et al.

(10) Patent No.: US 8,541,237 B2
(45) Date of Patent: Sep. 24, 2013

(54) METHOD FOR DIAGNOSING DISEASE USING ADENOVIRUS HARBORING TRANS-SPLICING RIBOZYME BY MOLECULAR IMAGING

(75) Inventors: In-Hoo Kim, Goyang-si (KR); Seong-Wook Lee, Seoul (KR); Seung-Hee Hong, Uijeongbu-si (KR); Jin-Sook Jeong, Busan (KR); Yoon-Jong Lee, Bucheon-si (KR); Yeon-Su Lee, Goyang-si (KR); Haeng-Im Jung, Goyang-si (KR)

(73) Assignee: National Cancer Center (KR)

( * ) Notice: Subject to any disclaimer, the term of this patent is extended or adjusted under 35 U.S.C. 154(b) by 126 days.

(21) Appl. No.: 12/522,597

(22) PCT Filed: Oct. 26, 2007

(86) PCT No.: PCT/KR2007/005334
§ 371 (c)(1),
(2), (4) Date: May 24, 2010

(87) PCT Pub. No.: WO2009/054558
PCT Pub. Date: Apr. 30, 2009

(65) Prior Publication Data
US 2011/0165690 A1    Jul. 7, 2011

(30) Foreign Application Priority Data
Oct. 25, 2007  (KR) .................. 10-2007-0107828

(51) Int. Cl.
*C12N 15/00* (2006.01)
*C12N 15/87* (2006.01)
*A61K 48/00* (2006.01)

(52) U.S. Cl.
USPC .................. 435/455; 514/44 R; 435/463

(58) Field of Classification Search
None
See application file for complete search history.

(56) References Cited

U.S. PATENT DOCUMENTS
2004/0018520 A1 * 1/2004 Thompson ............... 435/6
2004/0248141 A1   12/2004 Mitchell et al.

FOREIGN PATENT DOCUMENTS
WO    WO 03/066858    8/2003

OTHER PUBLICATIONS

Ayre et al., Optimization of trans-splicing ribozyme efficiency and specificity by in vivo genetic selection; NAR, vol. 30, No. 24, e141 pp. 1-9, 2002.*
Bhaumik et al., Molecular imaging of gene expression in living subjects by spliceosome-mediated RNA trans-splicing; PNAS, vol. 101, No. 23, pp. 8593-8698, 2004.*
Hong et al., Molecular imaging of endogenous mRNA expression in a mouse tumor model by adenovirus harboring trans-splicing ribozyme; FEBS Letters, vol. 581, pp. 5396-5400, 2007.*
Jin et al., Identification of a mouse cytoskeleton-associated protein, CKAP2, with microtubule-stabilizing properties; Cancer Sci, vol. 95, No. 10, pp. 815-821, 2004.*
Suzuki et al., Adenovirus-mediated ribozyme targeting of HER-2/neu inhibits in vivo growth of breast cancer cells; Gene Therapy, vol. 7, pp. 241-248, 2000.*
Kim et al., Selective Regression of Cells Expressing Mouse Cytoskeleton-Associated Protein 2 Transcript by Trans-Splicing Ribozyme; Oligonucleotides, vol. 17, pp. 95-103, 2007.*
Momota et al., Bioluminescence technology for imaging cell proliferation; Current Opinion in Biotechnology, vol. 16, pp. 681-686, 2005.*
Kobayashi, K. et al., "Reversal of Hypercholesterolemia in Low Density Lipoprotein Receptor Knockout Mice by Adenovirus-mediated Gene Transfer of the Very Low Density Lipoprotein Receptor", Journal of Biological Chemistry, vol. 271, No. 12, Issue of Mar. 22, pp. 6852-6860, 1996.
Lan N. et al., Ribozyme-Mediated Repair of Sickle β-Globin mRNAs in Erythrocyte Precursors, Science 280: 1593-1596; 1998.
Phylactou, L.A. et al., "Ribozyme-mediated *trans*-splicing of a trinucleotide repeat", Nature Genetics, vol. 18, 378-381, 1998.
Rogers, C.S., et al., "Functional repair of a mutant chloride channel using a *trans*-splicing ribozyme", The Journal of Clinical Investigation, vol. 110, pp. 1783-1789, 2002.
Ryu, K.J., et al., "Ribozyme-Mediated Selective Induction of New Gene Activity in Hepatitis C Virus Internal Ribosome entry Site-Expressing Cells by Targed *Trans*-Splicing", Molecular Therapy, vol. 7, No. 3, pp. 824-834, Mar. 2003.
Bhaumik, S. et al., "Molecular Imaging of Gene Expression in Living Subjects by Spliceosome-mediated RNA Trans-Splicing", PNAS vol. 101 (23), pp. 8693-8698, Jun. 8, 2004.
Shin, K.S., et al., Ribozyme-Mediated Induction of Apoptosis in Human Cancer Cells by Targeted Repair of Mutant p53 RNA, Molecular Therapy, vol. 10, No. 2, Aug. 2004.
Kwon, B.S. et al., "Specific Regression of Human Cancer Cells by Ribozyme-Mediated Targeted Replacement of Tumor-Specific Transcript", Molecular Therapy, vol. 12, No. 5, pp. 824-834, Nov. 2005.
Hasegawa, S. et al., "Detection of mRNA in Mammalian Cells With a Split Ribozyme Reporter", Chembiochem, vol. 7(6), pp. 925-928, Jun. 1, 2006.
Kim, Areum et al., Selective Regression of Cells Expressing Mouse Cytoskeleton-Associated Protein 2 Transcript by *Trans*-Splicing Ribozyme, Oligonucleotides, vol. 17, No. 1, Apr. 26, 2007, pp. 95-103, XP002630649, ISSN: 1545-4576.
Hong S-H et al., "In Vivo reprogramming of hTERT by trans-splicing ribozyme to target tumor cells", Molecular Therapy 200801 GB LNKD-DOI:10.1038/SJ.MT.6300282, vol. 16, No. 1, Aug. 14, 2007, pp. 74-80, XP002630648, ISSN:1525-0016.

(Continued)

*Primary Examiner* — Celine Qian
*Assistant Examiner* — Addison D Ault
(74) *Attorney, Agent, or Firm* — Brinks Hofer Gilson & Lione

(57) ABSTRACT

Disclosed herein is a composition for molecular imaging comprising a trans-splicing ribozyme coupled with an imaging reporter gene. The trans-splicing ribozyme targets a specific gene associated with a disease. Also disclosed is a molecular imaging method using the composition.

3 Claims, 14 Drawing Sheets

(56) References Cited

OTHER PUBLICATIONS

Hong, SH et al., "Molecular Imaging of Endogenous mRNA Expression in a Mouse Tumor Model by Adenovirus Harboring Trans-Splicing Ribozyme" *FEBS Lett.*, vol. 581(28), pp. 5396-5400, Nov. 27, 2007.

International Search Report for PCT/KR2007/005334, dated Jul. 25, 2008, 4 pages.

Supplementary European Search Report for EP Appln. No. 07833642.7 dated Mar. 30, 2011, (6 pages).

* cited by examiner

METHOD FOR DIAGNOSING DISEASE USING ADENOVIRUS HARBORING TRANS-SPLICING RIBOZYME BY MOLECULAR IMAGING

This application claims priority to PCT Application Ser. No. PCT/KR2007/005334 filed Oct. 26, 2007 published in English on Apr. 30, 2009 as PCT WO 2009/054558 and also to Korean Application No. 10-2007-0107828 filed Oct. 25, 2007, the entire contents of each are incorporated herein by reference.

TECHNICAL FIELD

The present invention relates to a composition for molecular imaging comprising a ribozyme and a molecular imaging method using said composition. More particularly, the present invention relates to a composition for molecular imaging comprising a trans-splicing ribozyme coupled with an imaging reporter gene and targeting a specific gene associated with a disease, and a molecular imaging method using the composition.

BACKGROUND ART

Ribozymes are RNA molecules having enzymatic activity. They have been voluntarily implicated in gene expression and control, such as RNA splicing, RNA processing, RNA genome replication and ribosomal peptide-bond formation. In particular, the group I intron ribozyme from *Tetrahymena thermophila* can join together two exons flanking the intron via the natural cis-splicing, and also can perform trans-splicing reactions to join two exons contained on separate RNAs. The trans-splicing proceeds via a cleavage-ligation reaction through a two-step transesterification mechanism. The ribozyme recognizes and binds a separate substrate RNA (5' exon) by forming base pairs between the target RNA and its internal guide sequence (IGS). Once bound, the ribozyme cleaves the targeted RNA, releases the downstream cleavage product and splices an exon sequence at its 3' end onto the 5' exon cleavage product of the substrate RNA instead of a cleaved 5' exon RNA region of its self-splicing process. This splicing occurs in *E. coli* and mammalian cells, as well as in vitro. The trans-splicing reaction can be applied for targeting and cleaving a specific target RNA and replacing it with a desired RNA sequence. Thus, trans-splicing ribozymes have the potential as novel therapeutic genes, which are capable of repairing defective RNA transcripts associated with genetic diseases with normal RNAs, or of targeting a specific RNA to express a desired RNA only within cells expressing the target RNA.

For example, a group I intron-based trans-splicing ribozyme has been shown to convert sickle $\beta^s$-globin transcripts into mRNAs encoding the anti-sickling protein γ-globin in erythrocyte precursors (Lan, N., et al., Science 280: 1593-1596. 1998). Also, a trans-splicing ribozyme was employed to amend a mutant myotonic dystrophy protein kinase transcript and a transcript of a mutant canine skeletal muscle chloride channel, causing myotonia congenita (Phylactou, L. A., et al., Nat. Genet. 18: 378-381, 1998; Rogers, C. S., et al., J. Clin. Invest. 110: 1783-1798, 2002). A trans-splicing ribozyme has been reported to induce the death of cancer cells by repairing mutant p53 transcripts with wild-type p53 transcripts (Shin, K. S., et al., Mol. Ther. 10: 365-372, 2004), and to block the replication of hepatitis C virus (HCV) by recognizing a specific region of HCV RNA genome and replacing it with RNA expressing anti-viral activity (Ryu, K. J., et al., Mol. Ther. 7: 386-395, 2003). Recently, many studies involve the potential of trans-splicing ribozymes as therapeutic genes for genetic diseases. For example, the expression of a hTERT-targeting group I intron-based trans-splicing ribozyme has been shown to induce the selective cytotoxicity in tumor cells expressing human telomerase reverse transcriptase (hTERT), and to have effective anticancer activity in an animal model implanted with human carcinoma cells (Kwon, B. S., et al., Mol. Ther. 12: 824-834, 2005). However, there are no reports describing the application of ribozymes as biosensor molecules and imaging agents for screening specific ligands and for use in the diagnosis of diseases. The present invention is the first to establish the above use of ribozymes.

Precise diagnosis of diseases is essential for successful gene therapy. Early diagnosis in particular is very critical for the successful treatment of diseases. Imaging technology and chemical and biological markers have been used for the early diagnosis of diseases, especially cancer. However, diagnostic imaging is disadvantageous in that it is unable to be used in the early stages. Chemical and biological markers exhibit low diagnostic accuracy, and thus, standard methods for early diagnosis using these markers have not been established. In particular, for gene-associated diseases, such as cancer, since there are no methods capable of monitoring the expression of associated genes in vivo, diseases can be detected when the body's response to diseases occurs only after an inordinate amount of time has passed since the associated genes began expression. Thus, diseases such as cancer are rarely curable in their early stages. Also, since the progression of diseases or responses to treatment after surgery or therapy is impossible to be monitored in the early stages in which gene expression occurs and can be monitored only when visual responses occur in the body, it is very difficult to perform a treatment which is optimal for individual patients. Various imaging methods, such as X-ray, CT, MRI, SPECT, PET and sonography, have been used for diagnosing cancer or genetic diseases. An image of a target site is assessed to determine whether it is cancerous in practice through pathological evaluation of a tissue sample isolated using invasive biopsy. However, when a tissue biopsy cannot be taken, interpretation of the image is difficult. Also, for treatment, tumor excision should be performed when a tumor increases to a size in which it can be excised thorough a surgery, thereby delaying diagnosis and not enabling proper treatment at the early stages.

Molecular imaging is a new approach that visualizes, through imaging, various molecular events occurring in cells, that is, gene expression, biochemical processes and biological changes. Molecular imaging enables doctors to determine the onset of cancer or other diseases in images of target tissues, and thus allows the non-invasive monitoring of suitable early treatment and non-surgical treatment without tissue biopsy. A composition for molecular imaging and a molecular imaging method according to the present invention have advantages overcoming disadvantages of existing molecular imaging technology, and harbor location signal accuracy and high temporal resolution, which will be needed in gene therapy and imaging technology in the future. Also, the composition and method of the present invention have beneficial clinical applications because a material used in molecular imaging does not have harmful side-effects, which it has not been possible yet to eradicate from molecular imaging employing quantum dot nanoparticles, which have been studied as a future technology.

DISCLOSURE

Technical Problem

Accordingly, the inventors of this application conducted thorough and intensive research into the application of trans-splicing ribozymes to molecular imaging. The research resulted in the finding that, when molecular imaging is performed using trans-splicing ribozymes targeting specific disease-associated genes, images obtained enable non-invasive and precise detection of the expression of disease-causing genes in vivo, indicating that the molecular imaging method of the present invention is excellent in diagnosing diseases earlier than conventional methods, thereby leading to the present invention.

Technical Solution

It is an object of the present invention to provide a composition for molecular imaging comprising a ribozyme vector targeting a specific gene.

It is another object of the present invention to provide a molecular imaging method based on using a ribozyme vector targeting a specific gene.

BEST MODE

In one aspect, the present invention relates to a composition for molecular imaging comprising a ribozyme vector targeting a specific gene.

As used herein, the term "ribozyme" refers to a RNA molecule that naturally harbors enzymatic activity, and preferably means a ribozyme having trans-splicing activity, and more preferably a trans-splicing ribozyme targeting a specific disease-associated gene.

Figure 1:
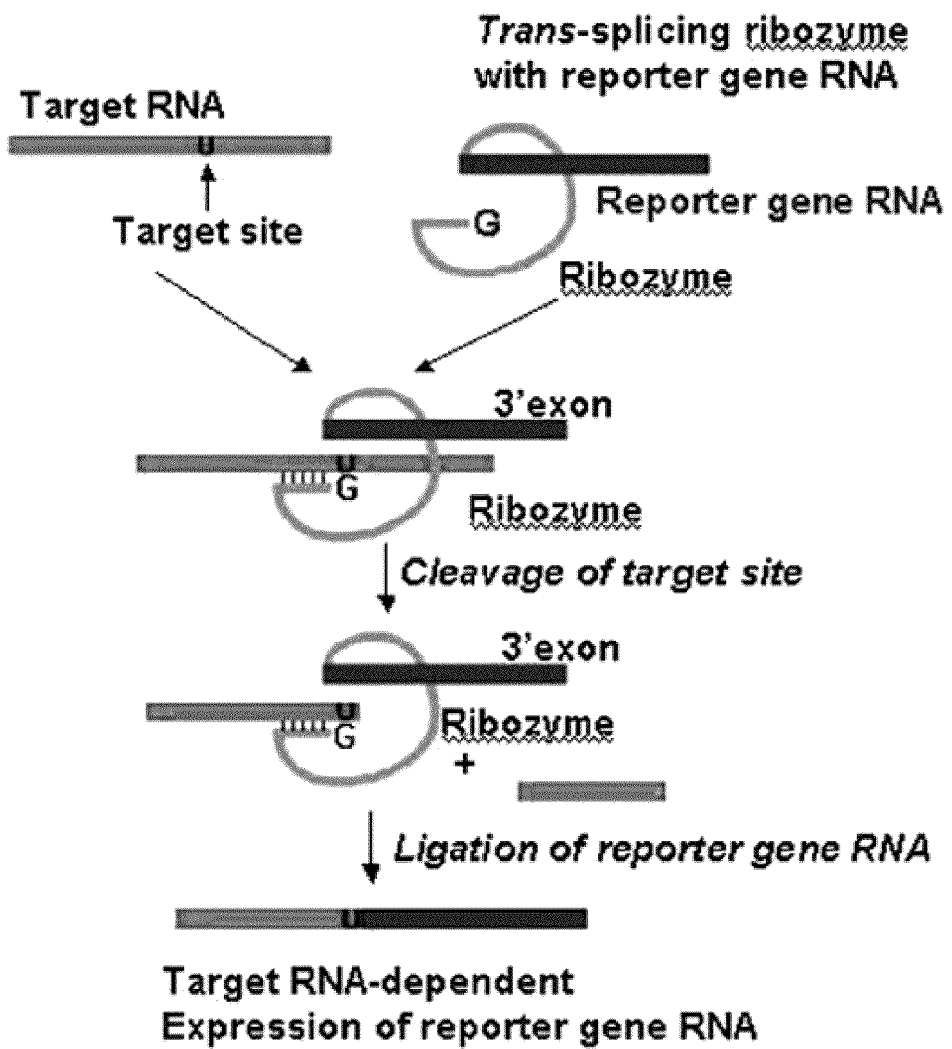
FIG. 1 schematically illustrates the trans-splicing mechanism of a ribozyme.

As used herein, the term "trans-splicing ribozyme" refers to a ribozyme having trans-splicing activity, with which the ribozyme recognizes a separate target RNA (5' exon) by forming base pairs between the target RNA and its internal guide sequence (IGS), cleaves the targeted RNA, and ligates a 3' exon of the ribozyme to the 5' exon cleavage product of the target RNA (FIG. 1). Also, the term "trans-splicing ribozyme targeting a specific gene" refers to a ribozyme that is genetically manipulated to recognize a specific gene associated with a disease and to induce selective trans-splicing reactions when introduced into cells. The trans-splicing ribozyme may be constructed using a method well known in the art. For example, such a ribozyme may be prepared to have substrate specificity for targeting a specific RNA by coupling a specific sequence complementary to a conserved region of a target (substrate) RNA to a 5' end of a ribozyme.

A modified trans-splicing ribozyme targeting a specific gene, suitable for use in the present invention, may be constructed in the form that an imaging reporter gene, encoding a protein allowing imaging by generating a bioluminescence reaction in vivo, is coupled to its 3' exon. When a trans-splicing ribozyme according to the present invention cleaves a target RNA, RNA bases downstream from the cleavage site are released. Then, a 3' region of the ribozyme is ligated to a 3' end of the cleavage product of the target RNA to fuse an imaging reporter gene to the ribozyme. The ribozyme fused with an imaging reporter gene enables the imaging and monitoring of the expression of a specific gene through molecular imaging. The imaging reporter gene is not particularly restricted if it is capable of monitoring images obtained through molecular imaging. Non-limiting examples of imaging reporter genes include fluorescent proteins, such as green fluorescent protein (GFP), modified green fluorescent protein, enhanced green fluorescent protein (EGFP), red fluorescent protein (RFP), enhanced red fluorescent protein (ERFP), blue fluorescent protein (BFP), enhanced blue fluorescent protein (EBFP), yellow fluorescent protein (YFP), enhanced yellow fluorescent protein (EYFP), cyan fluorescent protein (CFP), and enhanced cyan fluorescent protein (ECFP); and colorimetric enzymes, such as horseradish peroxidase (HRP), alkaline phoshpatase (AP), and luciferase. Luciferase is preferred.

As used herein, the term "recombinant vector", which describes a vector capable of expressing a protein of interest in a suitable host cell, refers to a genetic construct that comprises essential regulatory elements to which a gene insert is operably linked in such a manner as to be expressed in a host cell. The term "operably linked", as used herein, refers to a functional linkage between a nucleic acid expression control sequence and a nucleic acid sequence coding for a target protein in such a manner as to allow general functions. For example, when a ribozyme-coding sequence is operably linked to a promoter, the expression of the ribozyme-coding sequence is placed under the influence or control of the promoter. Two nucleic acid sequences (a ribozyme-coding sequence and a promoter region sequence linked to the 5' end of the coding sequence) are said to be operably linked if the induction of promoter function results in the transcription of the ribozyme-coding sequence, and if the nature of the linkage between the two DNA sequences does not result in the introduction of a frame-shift mutation nor interfere with the ability of the expression regulatory sequences to direct the expression of the ribozyme. The operable linkage to a recombinant vector may be prepared using a genetic recombinant technique well known in the art, and site-specific DNA cleavage and ligation may be easily achieved using enzymes generally known in the art A suitable expression vector in the present invention includes expression regulatory elements, such as a promoter, an initiation codon, a stop codon, a polyadenylation signal and an enhancer, as well as signal sequences for membrane targeting or secretion. Promoters may be generally constitutive or inducible. An expression vector may include a selectable marker that allows selection of host cells containing the vector, and a replicable expression vector may include a replication origin. The vector may be self-replicated or integrated into host DNA. Examples of vectors suitable for use in the present invention include, but are not limited to, plasmid vectors, cosmid vectors, and viral vectors. Viral vectors are preferred. Examples of viral vectors include, but are not limited to, vectors derived from retrovirus, such as human immunodeficiency virus (HIV) murine leukemia virus (MLV), avian sarcoma/leucosis virus (ASLV), spleen necrosis virus (SNV), rows sarcoma virus (RSV), and mouse mammary tumor virus (MMTV), adenovirus, adeno-associated virus, and herpes simplex virus. Adenovirus vectors are preferred.

Figure 3:
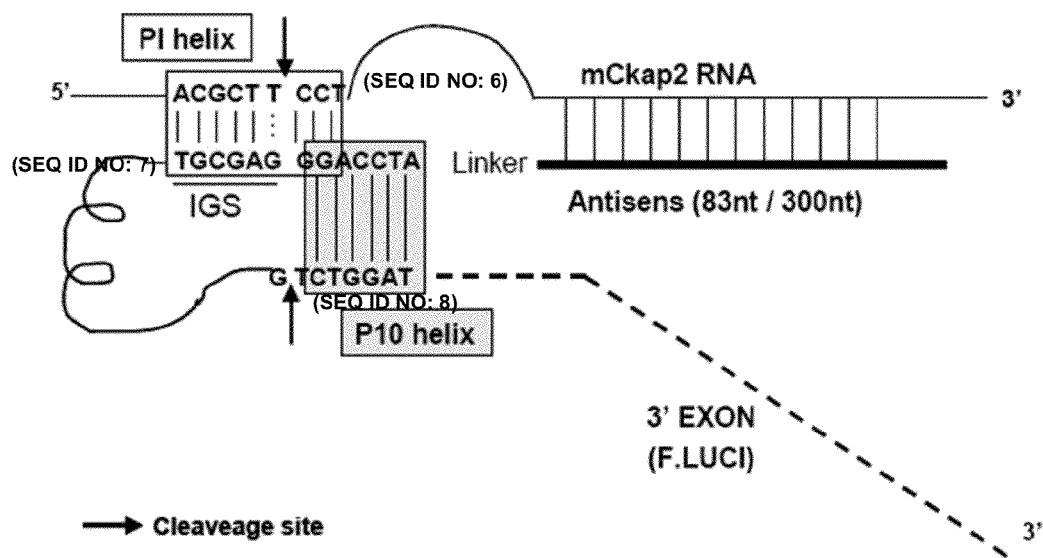
FIG. 3 shows the schematic structure of a modified ribozyme targeting a cancer-specific gene, mCKAP2, and carrying a luciferase gene.

In an embodiment of the present invention, an imaging reporter gene is coupled to a modified ribozyme targeting mouse cytoskeleton-associated protein 2 (mCKAP2) (Kim, A., et al., Oligonucleotides 17, 95-103, 2007). CKAP2, which serves as a microtubule stabilizer, is highly expressed in highly proliferative cells, such as cancer cells, and thus has been considered as a potential target for treating and diagnosing cancer. In detail, the ribozyme according to an embodiment of the present invention is a modified form of the trans-splicing group I ribozyme of *Tetrahymena thermophila*, and comprises 1) an antisense sequence complementary to a downstream region of an uridine residue (45U) of a target mCKAP2 RNA, the antisense sequence consisting of 83 nucleotides (complementary to nucleotides at positions +59 to +141 of mCKAP2 RNA) or 300 nucleotides (complementary to nucleotides at positions +59 to +358 of mCKAP2 RNA); 2) a P1 helix region linked to a 3' end of the antisense sequence and containing an internal guide sequence (IGS), 5'-GAGCGT-3'; 3) a P10 helix region linked to a 3' end of the P1 helix region; and 4) a sequence linked to a 3' end of the P10 helix region and encoding β-galactosidase (lacZ) or luciferase (luc). The schematic structure of the ribozyme is shown in FIG. 3. However, the present invention is not limited to the group I intron of *T. thermophila*, and other group I introns may be employed to construct a ribozyme according to the present invention based on the above criteria and information known in the art by those skilled in the art. The ribozyme contained in the present composition replaces a target gene, that is, a disease-associated gene with an imaging reporter gene through a trans-splicing reaction, thereby enabling molecular imaging. Thus, the ribozyme of the present invention is very useful in the diagnosis of diseases associated with genes through the use of molecular imaging.

The term "molecular imaging" refers to a technology that evaluates various molecular events occurring in cells, that is, gene expression, biochemical processes and biological changes through imaging. In particular, molecular imaging used in the present invention is meant to indicate gene imaging, which images the expression of a specific gene. Since the imaging technology evaluates images using an imaging reporter gene, it allows for the repetitive experiments to be conducted in a single individual while not severely harming experimental animals.

Imaging reporter genes making it possible to obtain images through molecular imaging include share similar characteristics with those described above, and images may be taken using a method widely known in the art. For example, when a luciferase gene is used, images may be obtained using a hypersensitive cooled charge-coupled device camera. As well, luciferase expression may be monitored through various molecular imaging techniques used in nuclear medicine imaging, such as infrared fluorescence imaging, optical diffusion tomography, optical coherence tomography, and positron emission tomography (PET).

As used herein, the term "gene-associated disease" is meant to include, but is not limited to, genetic disorders, such as polycystic kidney disease, multiple endocrine neoplasia type 1, neurofibromatose, Tay-sachs disease, Huntington's disease, sickle-cell anemia, thalassemia and Down's syndrome (The Metabolic and Molecular Bases of Inherited Disease, 7th ed., McGraw-Hill Inc., New York); and all diseases caused by genetic defects, such as cancer, hypertension, Alzheimer's disease, neurodegenerative disease, and neuropsychiatric disorders, such as bipolar affective disorder or paranoid schizophrenic disorder.

The "specific gene", targeted by the ribozyme of the present invention, refers to a gene that directly or indirectly participates in the onset, progression or treatment of diseases such as described above. In a detailed embodiment, CKAP2 was used, but the present invention is not limited thereto.

Figure 12:
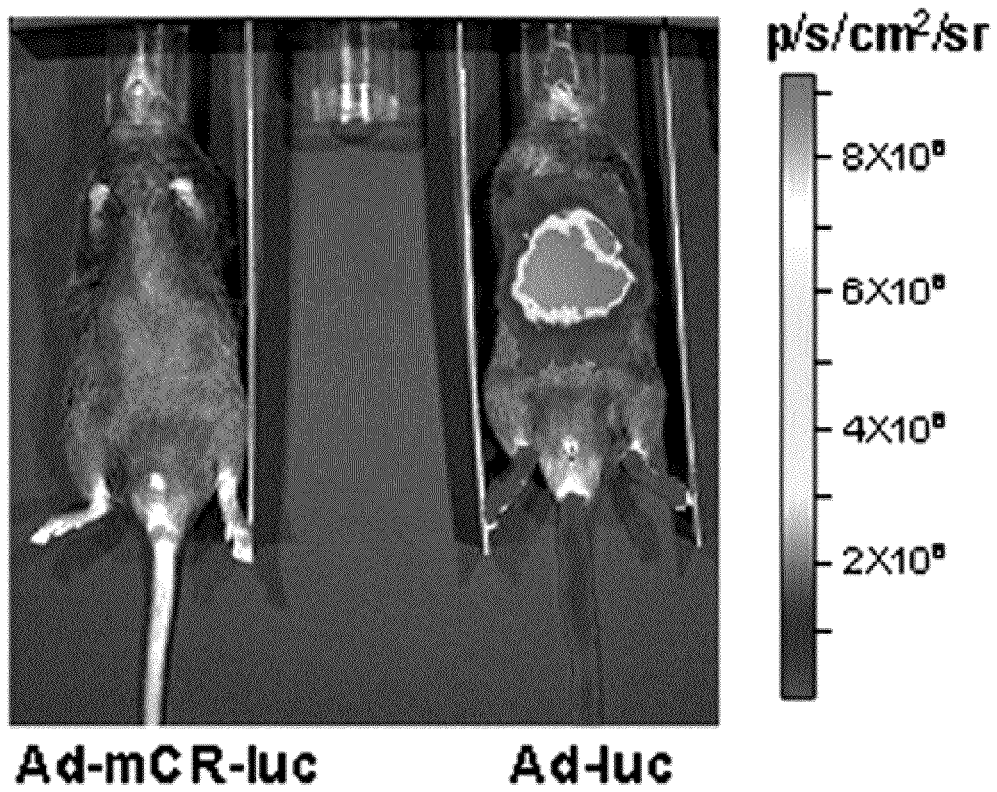
FIG. 12 shows the results of the imaging of mCKAP2 expression by a trans-splicing ribozyme in living mice. Bioluminescence signals generated by the systemically delivered Ad-mCR-luc in non-tumor-harboring mice were imaged using a CCD camera (the signal intensity was expressed in photon/second/$cm^2$/steridian).
Figure 13:
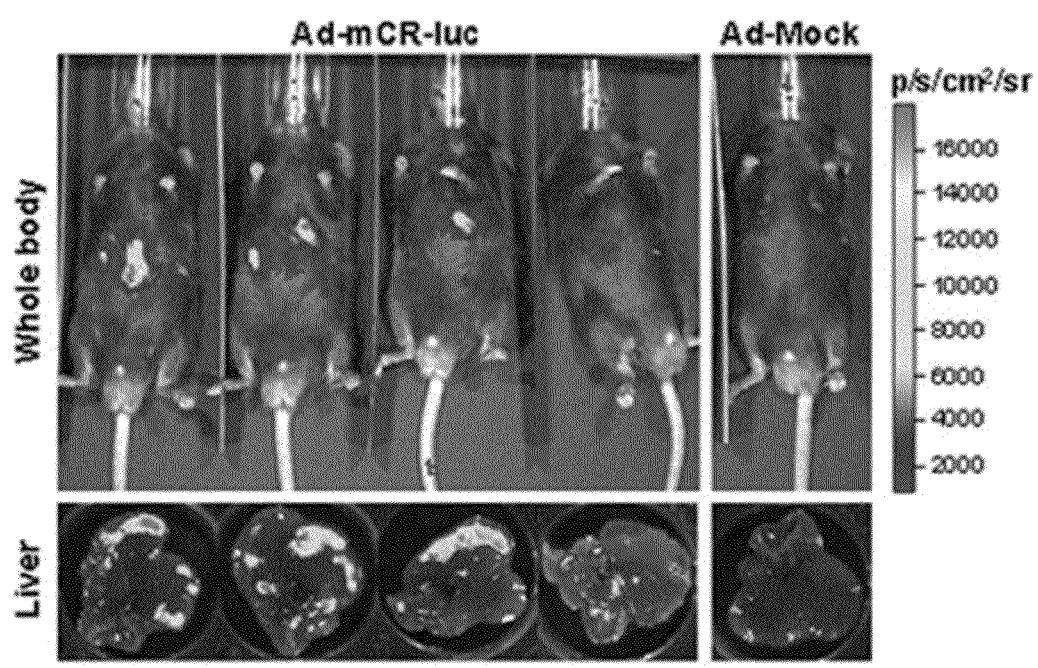
FIG. 13 shows the results of in vivo imaging of multiple hepatocellular tumors using Ad-mCR-luc. Images were obtained from mice harboring multiple hepatocellular tumors, which were injected with Ad-mCR-luc via tail veins. Direct images of tumor nodules in liver tissues excised from the mice are shown in the lower panel, and an image of a mouse injected with Ad-Mock as a negative control are shown in the right lower panel.
Figure 14:
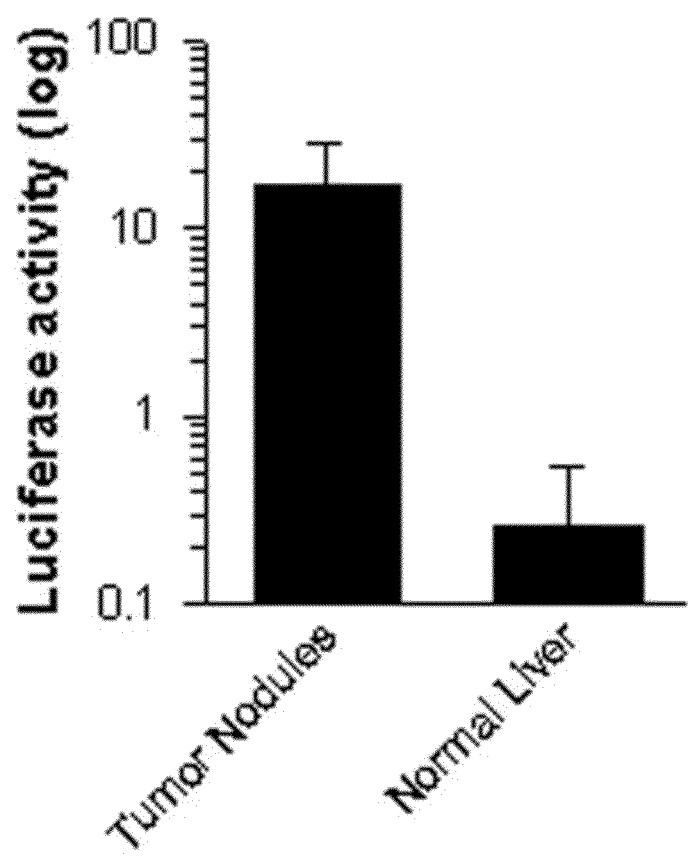
FIG. 14 shows the luciferase activity of tumor nodules from mice injected with Ad-mCR-luc. Luciferase expression was measured and expressed in RLU/s/μg protein in a log scale. Measurements were performed in triplicate, and means of measurements are shown as a graph with bars indicating standard error (SE).

In practice, when Hepa1-6 cells an adenovirus, Ad-mCR-lacZ or Ad-mCR-luc, which is prepared by coupling a beta-galactosidase or luciferase gene to the downstream of a trans-splicing ribozyme targeting mouse CKAP2, was transfected into a hepatocellular carcinoma cell line, Hepa1-6, the target gene was replaced with the reporter gene through CKAP2-specific trans-splicing (FIGS. 6 to 11). Also, when an adenovirus Ad-mCR-luc was administered to mice harboring hepatic tumors, molecular imaging of cancer in mice was achieved through luciferase expression (FIGS. 12 and 13).

In another aspect, the present invention relates to a method of preparing a vector for molecular imaging, comprising 1) linking an imaging reporter gene to a ribozyme targeting a specific gene, and cloning the resulting ribozyme; 2) inserting the cloned ribozyme into a vector and expressing the ribozyme; and 3) isolating the vector identified to express the ribozyme and confirming the ribozyme.

In a further aspect, the present invention relates to a molecular imaging method based on using a ribozyme vector targeting a specific gene.

In an embodiment, the method comprises 1) administering in vivo the vector of the present invention and allowing the ribozyme to function at an expression site of the target gene so as to activate an imaging reporter gene; and 2) imaging the activation of the imaging reporter gene through molecular imaging.

As used herein, the term "administration" means the introduction of a predetermined amount of a substance into a patient using a certain suitable method. The composition of the present invention may be formulated into dosage forms for use in humans or for veterinary use, and may be administered via any of the common routes. A viral vector may be administered via a parenteral route, for example, intravascularly, intravenously, intraarterially, intramuscularly or subcutaneously. As well, the composition may be administered orally, intranasally, intrarectally, intradermally, or via an inhalation route through aerosol. A viral vector may be administered as a bolus or slowly injected.

The molecular imaging of the activation of the imaging reporter gene may be performed using various molecular imaging methods, which are exemplarily described above, but the present invention is not limited to the examples. Also, the molecular imaging method according to the present invention may be used for diagnosing various diseases associated with genes, and such diseases are the same as described above.

[Mode for Invention]

A better understanding of the present invention may be obtained through the following examples which are set forth to illustrate, but are not to be construed as the limit of the present invention.

EXAMPLE 1

Figure 2:
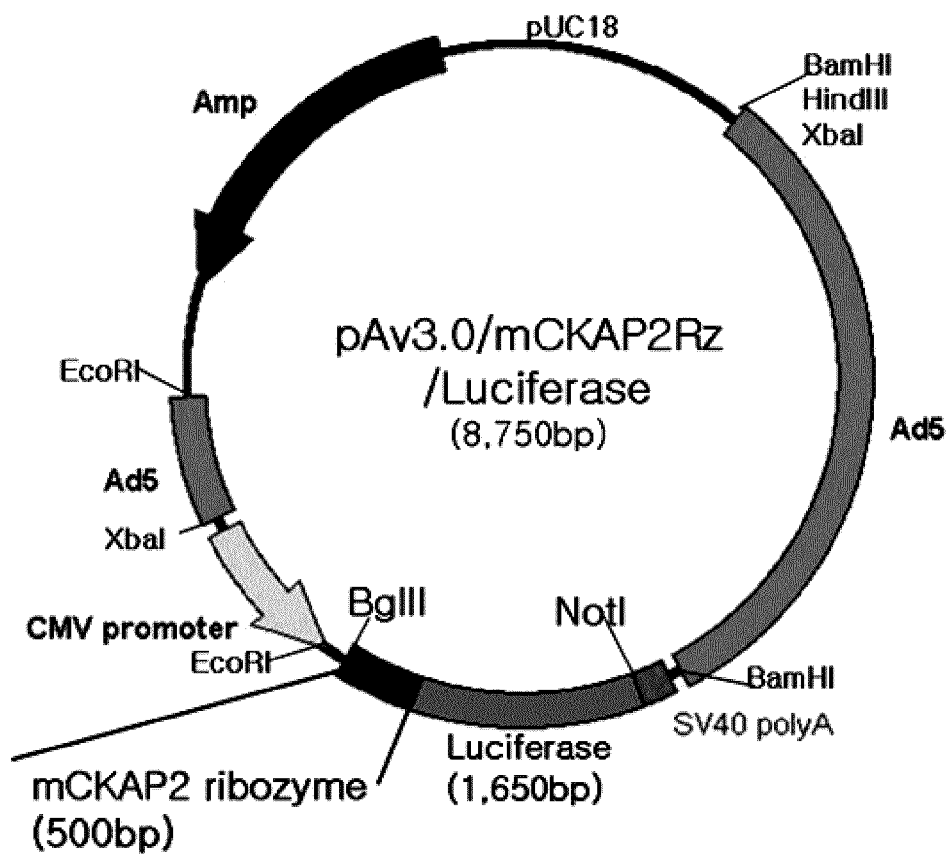
FIG. 2 shows the schematic map of an adenovirus vector Ad-mCR-luc, which targets a cancer-specific gene, mCKAP2, and carries a luciferase gene.

Preparation of Test Materials 1-1, Construction of Recombinant Adenovirus Expressing Cancer Gene-Specific Trans-Splicing Ribozyme A trans-splicing ribozyme targeting a cancer-specific gene mCKAP2 was constructed using a known technique (Kim, A., et al., Oligonucleotides 17:95-103, 2007). Abeta-galactosidase(lacZ) or luciferase (luc) gene was linked to a 3' of a ribozyme, and the resulting ribozyme was cloned. The ribozyme fused to the reporter gene was subcloned into BglII and NotI sites of a shuttle vector pAvCMV3.0 containing a CMV promoter. The shuttle vector was co-transfected into HEK293 cells with an adenoviral backbone vector, pJM17, cells using calcium-phosphate precipitation. Then, transfected cells were allowed to grow under soft agar for two weeks in order to form viral plaques. A multiple of clones were isolated. Recombinant viruses were amplified in HEK293 cells, and were purified using a known method, that is, through two rounds of CsCl gradient ultracentrifugation (Kobayashi, K., et al., J. Biol. Chem. 271:6852-6860, 1996). A purified recombinant adenovirus containing the trans-splicing ribozyme specifically targeting mCKAP2 and a lacZ gene was designated "Ad-mCR-lacZ". Another purified recombinant adenovirus containing the mCKAP2-specific trans-splicing ribozyme and a luc gene was designated"Ad-mCR-luc". The schematic map of Ad-mCR-luc is shown in FIG. 2. As a negative control, the adenovirus backbone vector (Ad-Mock) and adenovirus vectors carrying a lacZ gene (Ad-lacZ) and a luc gene (Ad-luc) were used. The titer of isolated recombinant adenovirus vectors was determined as a plaque forming unit (pfu) using a TCID50 method.

1-2, Cell Culture

Murine hepatocellular carcinoma Hepa1-6 cells, murine colon carcinoma CT-26 cells, murine fibroblast NIH3T3 cells, human hepatocellular carcinoma HepG2 cells, murine hepatocellular carcinoma BNL1MEA.7R.1 cells, and murine melanoma B16F10 cells were used. The cell lines were cultured in Dulbecco's modified Eagle's medium (DMEM; Gibco) supplemented with 10% fetal bovine serum (Invitrogen) and 100 U/mL of penicillin/streptomycin in an incubator at 37° C. under 5% $CO_2$.

1-3, Preparation of an Animal Model of Hepatocellular Carcinoma 6- to 8-week-old male C57BL6 mice were purchased from the Orient Company (Seoul, Korea). The animals were maintained under pathogen-free conditions in an animal experiment room of the Korea Food & Drug Administration, and were acclimated to experimental conditions for at least one week before use. The animals were exposed to a regular 12-h light/dark cycle, with lights on at 6:00 am and lights off at 6:00 pm.

An animal model of hepatocelluar carcinoma was established by injecting Hepa1-6 cells into the spleen of mice through a slight modification of a known method (Giavazzi, R., et al., J Natl Cancer Inst 77:1303-8, 1986). In brief, Hepa1-6 cells were fluently cultured in culture dishes and subcultured the day before being injected to mice. Hepa1-6 cells were harvested with 0.025% trypsin-EDTA and washed with PBS three times. Cells were stained with trypan blue, and the number of viable cells was counted. When viable cells were higher than 95%, the cultured cells were injected to mice. Hepa1-6 cells were suspended at a density of $2 \times 10^6$ cells/50 µl. A small longitudinal left flank incision was made to expose the spleen, and $2 \times 10^6$ cells in a 50-µl volume were slowly injected into the spleen with a 29-guage needle. After the needle was removed, the spleen was returned to the abdominal cavity, and the abdominal incision was closed with a silk suture. Within 8 to 10 days after the injection of Hepa1-6 cells, multiple tumor nodules were readily detectable in the liver through general observation.

EXAMPLE 2

In Vitro Diagnosis of Cancer Cells through Molecular Imaging Using Trans-Splicing Ribozyme (Ad-mCKAP2-lacZ)

2-1, Evaluation of mCKAP2 Expression in Mouse Tissues or Cell Lines

Western blot analysis was performed in order to determine whether the mCKAP2 protein is expressed in mouse tissues or cell lines. Total RNA was isolated from mouse tissues or each organ using Trizol Reagent (Invitrogen), and treated with RQ1 RNase-free DNase I (1 U/μg RNA; Promega) in RNase-free water and buffer at 37° C. for 30 min. For cDNA synthesis, a reaction mixture was prepared with the DNase I-treated total RNA, 4 U of reverse transcriptase (Omniscript-RTase, Qiagen), dNTP Mix, 10×RT buffer, 250 ng of random primer (Invitrogen), and 40 U of RNase Inhibitor. Reverse transcription was carried out under conditions including 10 min at 25° C., 1 hr at 37° C., and heating at 95° C. for enzyme inactivation. Using the synthesized cDNA as a template, mCKAP2 was amplified using mCKAP2-specific primers, summarized in Table 1, below, and a reaction mixture under reaction conditions, described below. The expression of the mCKAP2 gene was detected through agarose gel electrophoresis.

TABLE 1

| Primers | Sequences |
|---------|-----------|
| mCKAP2 forward | 5'-GGGAGATCTATGGCAGAGTCCAGGAAACGCTTC-3' (SEQ ID No. 1) |
| mCKAP2 reverse | 5'-CACAGTCTGACCTGGCAAATCATCTCTTG-3' (SEQ ID No. 2) |
| mCKAP2 UTR primer | 5'-AAAGGATCCAGGCGCGCTCATTAAGCGATGG-3' (SEQ ID No. 3) |
| lacZ reverse | 5'-GGGCTCGAGCGGATTGACCGTAATGGA-3' (SEQ ID No. 4) |

PCR Reaction Mixture

| | |
|---|---|
| Water (HPLC grade) | 14.40 μL |
| 10× buffer (15 mM MgCl$_2$, 25 mM MgCl$_2$) | 2.00 μL |
| dNTP Mix (Dakara) (25 mM/each) | 1.60 μL |
| Taq pol(5 U/μl; Dakara) | 0.20 μL |
| Forward/reverse primer mix | 0.80 μL |
| cDNA | 1.00 μL |
| Total volume | 20.00 μL |

PCR conditions included 5 min at 95° C. and 30 cycles of 30 sec at 95° C., 30 sec at 65° C. and 1 min at 72° C., followed by cooling to 4° C.

Figure 4:
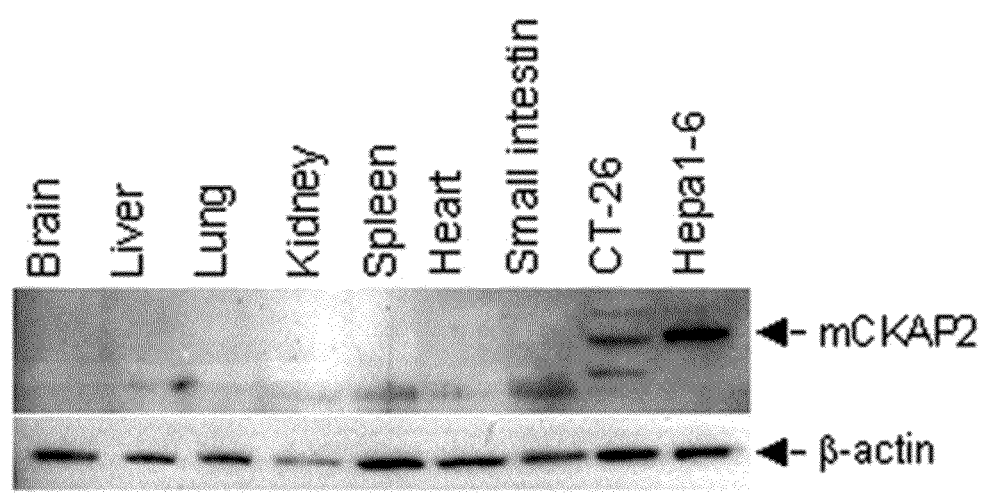
FIG. 4 shows the results of Western blotting for the expression patterns of the CKAP2 protein in various tissues of C57BL/6 mice (brain, liver, lung, kidney, spleen, heart and small intestine) and murine carcinoma cells, CT-26 and Hepa1-6.
Figure 5:
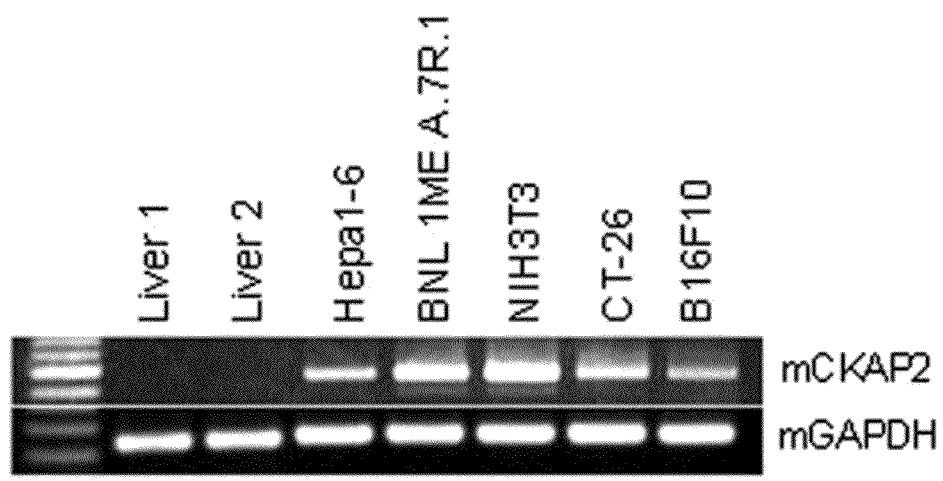
FIG. 5 shows the expression patterns of CKAP2 mRNA in mouse liver tissues and several murine carcinoma cells.

As a result, mCKAP2 was found to be expressed in murine carcinoma cell lines, CT-26 and Hepa1-6 (FIGS. 4 and 5).

2-2, In Vitro Detection of mCKAP2 and Trans-Spliced Molecules Using RT-PCR

RT-PCR was performed to detect trans-spliced molecules (TSMs). CKAP2-retaining Hepa1-6 cells and CKAP2-deleted HepG2 cells were infected with a trans-splicing ribozyme-harboring adenovirus, Ad-mCR-lacZ, Ad-lacZ and Ad-Mock at 30 moi. Total RNA was isolated from the infected cells, and cDNAs were synthesized using the same method as described above. In order to assess the production of TSMs, using the synthesized cDNA as a template, TSMs were amplified using TSM-specific primers, summarized in Table 1 and the reaction mixture under the reaction conditions, described above (annealing was carried out at 60° C., and denaturation and elongation were carried out at the same temperature as described above). The forward and reverse primers were designed to amplify mCKAP2 or trans-spliced molecules. In particular, TSM-specific primers were designed to anneal to a mCKAP2 upstream region of a trans-splicing junction and to a downstream region of the trans-splicing junction.

Figure 6:
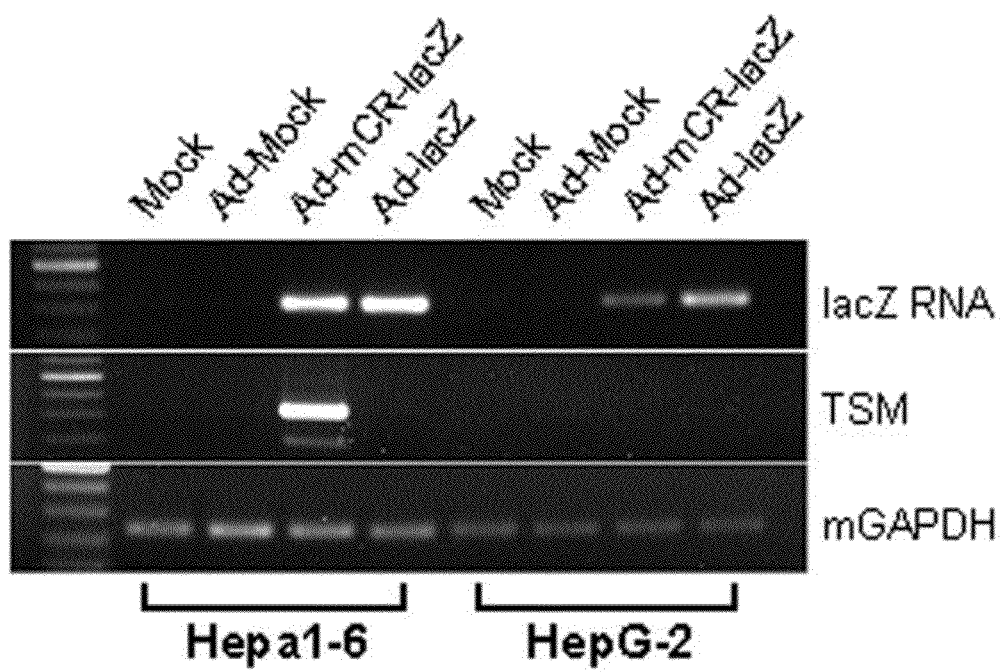
FIG. 6 shows the replacement of a target gene with a reporter gene through mCKAP2-specific trans-splicing after cells were transfected with Ad-mCR-lacZ. Hepa1-6 cells, harboring the mCKAP2 gene, and HepG2 cells, deleted in the mCKAP2 gene, trans-spliced molecules (TSMs) were detected using RT-PCR. As a negative control (Mock), an equal volume of PBS was used. The upper blot (LacZ RNA) shows the primary transcripts of the ribozyme transfected into cells. The middle blot (TSM) shows the transcripts produced by trans-spliced molecules. The lower blot (mGAPDH) shows the internal control for gene expression levels.

The results are given in FIG. 6. As shown in FIG. 6, when cells were transfected with Ad-mCR-lacZ, the target gene was found to be replaced with the reporter gene through mCKAP2-specific trans-splicing.

Figure 7:
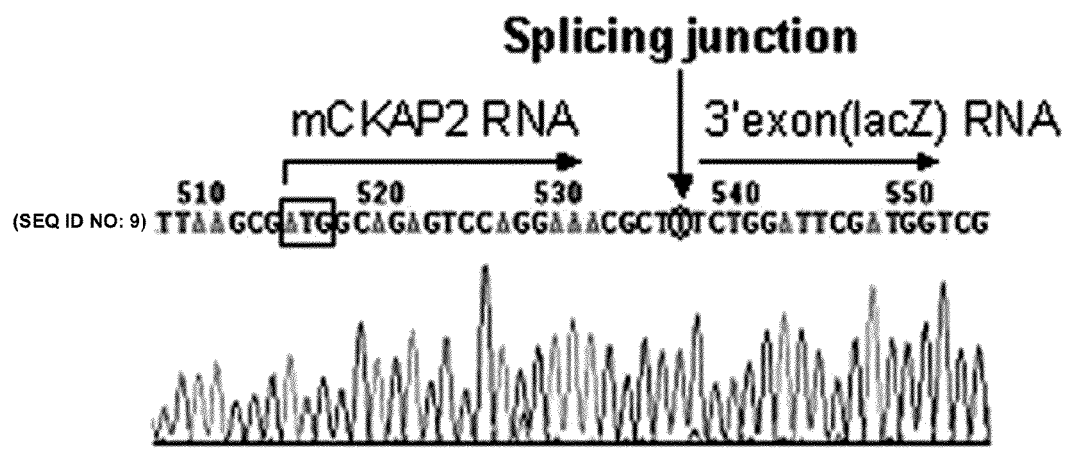
FIG. 7 shows the DNA sequencing analysis of a trans-spliced transcript in Hepa1-6 cells (an arrow indicates precise splicing junction).

In order to evaluate the specificity of the trans-splicing reaction of the ribozyme, the amplified products were purified using a PCR purification kit, cloned into BamHI/XhoI sites of pBluescript (SK+/−), and subjected to DNA sequencing analysis by the Macrogen Company (Korea) (FIG. 7).

2-3, β-Galactosidase Assay

In order to determine whether the ribozyme targets mCKAP2 and is expressed, cells were infected with the recombinant adenovirus Ad-mCR-lacZ, a lacZ gene is fused to the 3' end of a ribozyme gene. The expression of β-galactosidase was analyzed quantitatively through X-gal staining and a β-galactosidase assay. For X-gal staining, Hepa1-6 and HepG2 cells were seeded onto 6-well culture plates at a density of $2 \times 10^5$ cells/well, and cultured at 37° C. The next day, cells were infected with the Ad-mCR-lacZ adenovirus at a moi of 0, 10, 30 or 50, The Ad-lacZ adenovirus, carrying a lacZ gene under the control of a CMV promoter, was used as a positive control. Cells were infected with Ad-lacZ at 30 moi. After 48 hrs, cells were stained using a β-galactosidase staining kit (Invitrogen Corporation, CA, USA).

Figure 8:
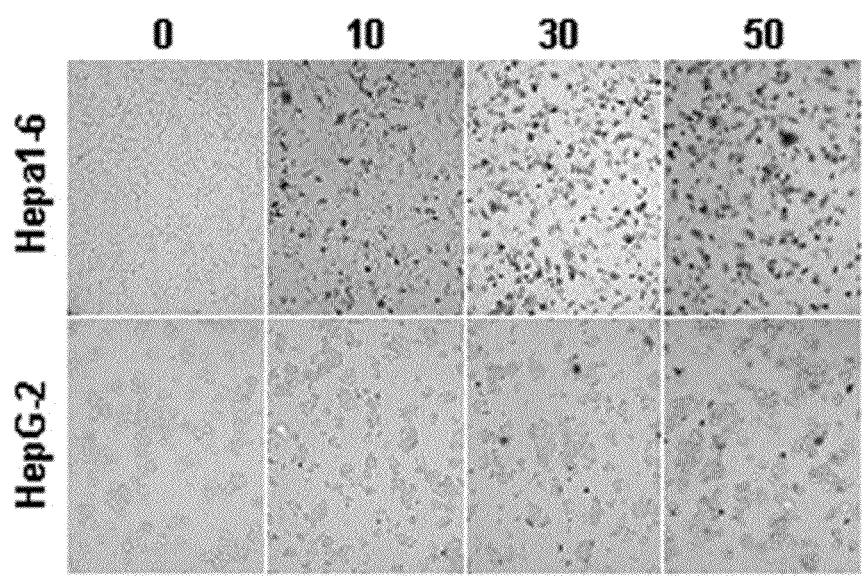
FIG. 8 shows the results of X-gal staining, in which a reporter gene (lacZ) was expressed in a mCKAP2 gene-specific manner by Ad-mCR-lacZ. Hepa1-6 and HepG2 cells were transfected with Ad-mCR-lacZ at a moi (multiplicity of infection) of 10, 30 or 50, and were stained with X-gal.

As shown in FIG. 8, when Hepa1-6 cells were transfected with the Ad-mCR-lacZ adenovirus harboring the mCKAP2 gene, the target gene was replaced with the lacZ gene through mCKAP2-specific trans-splicing, leading to high expression of β-galactosidase, encoded by the lacZ gene. The β-galactosidase expression increased with increasing doses of the adenovirus.

Separately, in order to assess β-galactosidase activity, cells were lysed with a lysis buffer (Promega). Protein concentrations were determined using a BCA protein assay kit (Pierce, Rockford, Ill., USA). The β-galactosidase (β-gal) activity was determined using a β-gal assay kit (Invitrogen). The specific activity of β-galactosidase was calculated according to the following equation.

Specific activity=nmoles of ONPG hydrolysed/min/mg protein

Figure 9:
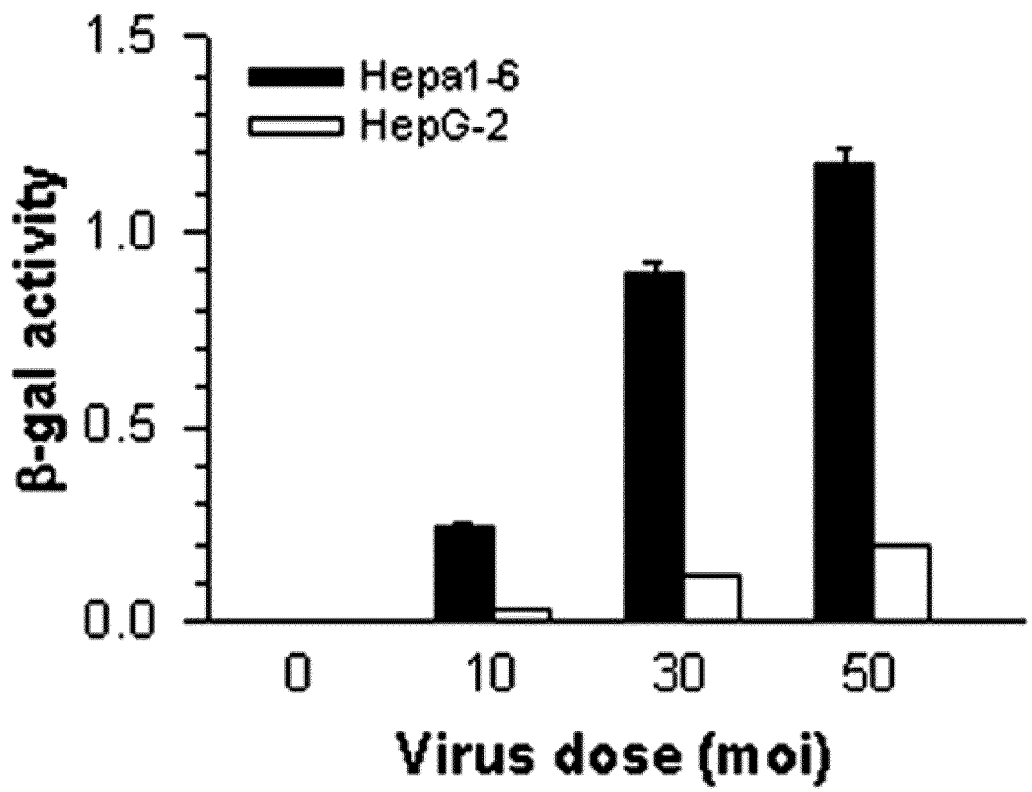
FIG. 9 shows the specific activity of β-galactosidase in Hepa1-6 and HepG2 cells transfected with Ad-mCR-lacZ. Measurements were performed in triplicate, and means of measurements are shown as a graph with bars indicating standard error (SE) (Specific activity=nmoles of ONPG hydrolysed/min/mg protein).

As shown in FIG. 9, β-gal activity was found to increase with increasing viral doses of Ad-mCR-lacZ.

EXAMPLE 3

In Vitro Diagnosis of Cancer Cells through Molecular Imaging Using Trans-Splicing Ribozyme (Ad-mCKAP2-luc)

3-1, Luciferase Assay

In order to assess luciferase expression, $1 \times 10^4$ Hepa1-6 cells were seeded onto black 96-well culture plates and cultured. The next day, cells were infected with the recombinant adenovirus Ad-mCR-luc, targeting mCKAP2 and expressing luciferase, and the Ad-luc adenovirus, carrying a luciferase gene under the control of a CMV promoter, at 0, 1, 5, 10, 15, 30 and 50 moi. After 5 hrs, cells were lysed with a lysis buffer (Promega). The luciferase activity was determined using a Blight-Glo™ luciferase assay system (Promega). The emitted light intensity was measured in relative light units (RLU) per 10 sec using a luminometer, and the measured values were expressed in RLU/s/μg protein.

Figure 10:
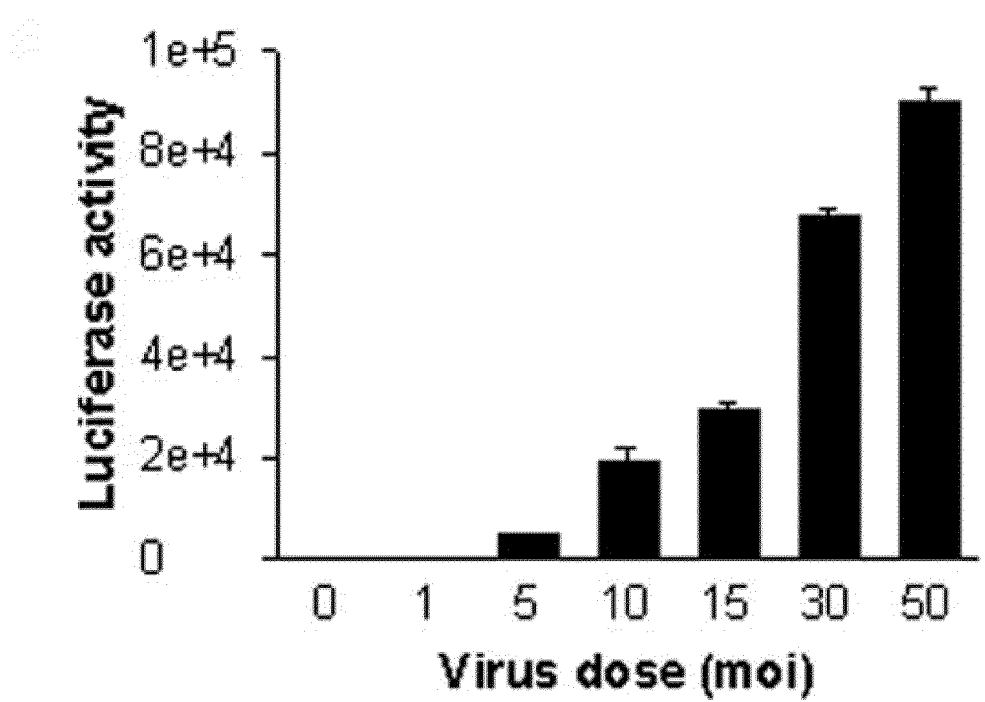
FIG. 10 shows the luciferase activity in Hepa1-6 cells transfected with Ad-mCR-luc according to viral doses. Measurements were shown as a graph with bars indicating standard error (SE).

As shown in FIG. 10, when Hepa1-6 cells were transfected with the Ad-mCR-luc adenovirus harboring the mCKAP2 gene, the target gene was replaced with the luc gene through mCKAP2-specific trans-splicing. The luciferase activity increased with increasing viral doses of Ad-mCR-luc.

3-2, Western Blot Analysis

Cells or mouse tissues were lysed with a protein extraction solution (Sigma), which contained 20 mM Tris-HCl (pH 7.5), 5 mM EDTA, 10 mM $Na_4P_2O_7$, 10 mM NaF, 2 mM $Na_3VO_4$, 1% NP-40, PMSF and protease inhibitor. Proteins were transferred onto a nitrocellulose membrane using a known method. In detail, purified proteins (25 μg or 50 μg) were separated by SDS-PAGE according to molecular size, and transferred onto a NC membrane (Millipore) using a blotting device. The blot was blocked with blocking buffer (5% skim milk in TBS containing 0.05% Tween 20) for 30 min. The blot was then incubated in a primary antibody, rabbit polyclonal anti-mCKAP2 antibody or anti-f3-actin antibody (Sigma), for 1 hr at room temperature or overnight at 4° C. The blot was washed with Tween tris-buffered saline (T-TBS) twice to remove unbound primary antibodies. The bound primary antibodies were probed with horseradish peroxidase-conjugated anti-rabbit antibody (Amersham).

Figure 11:
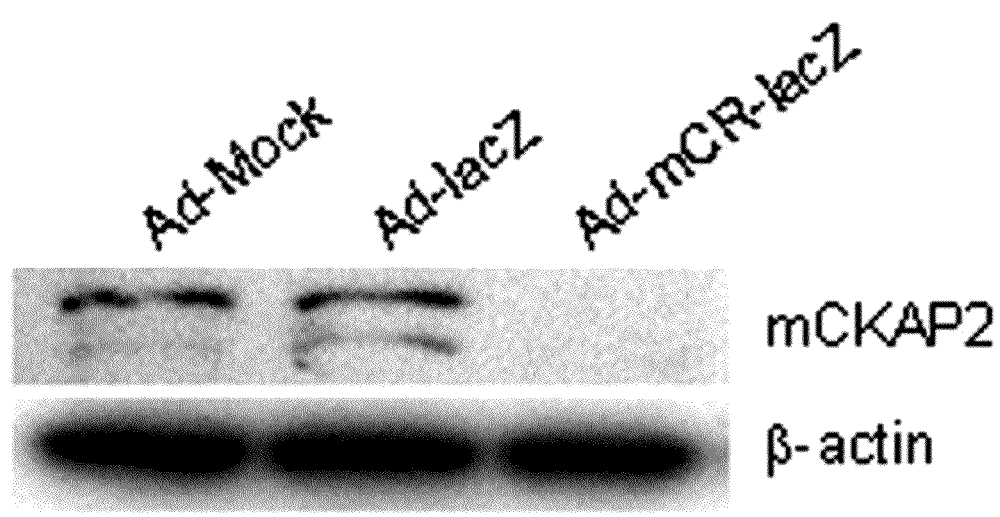
FIG. 11 shows the decreased expression of a target gene, mCKAP2, by the trans-splicing reaction of Ad-mCR-lacZ. The expression patterns of endogenous mCKAP2 was assessed through Western blotting 24 hrs after Hepa1-6 cells were transfected with Ad-Mock, Ad-lacZ and Ad-mCR-lacZ at a moi of 30, The upper and lower blots were probed with anti-mCKAP2 and anti-β-actin antibodies.

As shown in FIG. 11, when Hepa1-6 cells were transfected with the Ad-mCR-luc adenovirus harboring the mCKAP2 gene, the target gene was replaced with the luc gene through mCKAP2-specific trans-splicing, leading to decreased mCKAP2 expression.

EXAMPLE 4

In Vivo Diagnosis of Cancer through Molecular Imaging Using Trans-Splicing Ribozyme (Ad-mCKAP2-luc)

In vivo molecular imaging was performed using a Xenogen IVIS 2000 cooled CCD camera (Xenogen, Hopkinton, Mass.). The Ad-mCR-luc recombinant adenovirus, the Ad-luc adenovirus as a positive control, and the Ad-mock virus as a negative control were prepared at a viral dose of $10^{11}$ viral particles (vp) in 50 μL of Dulbecco's PBS (Life Technologies), and were systemically administered to mice through injection via tail veins. The next day, D-luciferin, a substrate of luciferase, in 200 μL of PBS was intraperitoneally administered to mice at a dose of 150 mg per kg mouse. For in vivo molecular imaging, mice were anesthetized with isofluran-mixed oxygen. After 10min, a reference image was taken, and in vivo images were taken for from 1 min to 5 min. Whole body imaging was performed using a Living Image Software (Xenogne), and the results were expressed in photon per second per $cm^2$ per steridian (p/s/$cm^2$/sr).

As shown in FIG. 13, the luciferase expression was found to enable the imaging of livers excised from Ad-mCR-luc-transfected mice having hepatocellular tumors.

INDUSTRIAL APPLICABILITY

As described hereinbefore, the molecular imaging method using a trans-splicing ribozyme according to the present invention enables precise diagnosis of diseases at early stages by providing for imaging the expression of a disease-associated gene at sites of gene expression. Also, the molecular imaging method may be useful in prognostic diagnosis and treatment of gene-associated diseases, for example, for evaluating therapeutic effects and responses to drugs.

The invention claimed is:

1. A method for molecular imaging of cancer cells in a subject, the method comprising:

1) administering to a subject a trans-splicing ribozyme vector comprising a trans-splicing ribozyme specific to a target gene and an imaging reporter gene, wherein upon administration, the target gene is replaced with the imaging reporter gene through ribozyme-mediated trans-splicing so as to activate the imaging reporter gene; and 2) analyzing the activation of the imaging reporter gene through molecular imaging, wherein the trans-splicing ribozyme is a modified form of a trans-splicing group I ribozyme and comprises:

i) an antisense sequence complementary to a region downstream of the uridine residue at position +45 of the target mouse cytoskeleton-associated protein 2 (mCKAP2) RNA, the antisense sequence consisting of 83 nucleotides complementary to nucleotides at positions +59 to +141 of mCKAP2 RNA or 300 nucleotides complementary to nucleotides at positions +59 to +358 of mCKAP2 RNA;

ii) a P1 helix region linked to the 3' end of the antisense sequence which comprises an internal guide sequence (IGS), 5'-GAGCGT-3';

iii) a P10 helix region linked to the 3' end of the P1 helix region; and iv) a sequence linked to the 3' end of the P10 helix region and encoding β-galactosidase (lacZ) or luciferase (luc).

2. The method according to claim 1, wherein the vector is an adenovirus vector.

3. The method according to claim 1, wherein the vector has a genetic map shown in FIG. 2.

* * * * *

SEQUENCE LISTING

```
<160> NUMBER OF SEQ ID NOS: 9

<210> SEQ ID NO 1
<211> LENGTH: 33
<212> TYPE: DNA
<213> ORGANISM: Artificial Sequence
<220> FEATURE:
<223> OTHER INFORMATION: synthetic mCKAP2 forward primer

<400> SEQUENCE: 1
gggagatcta tggcagagtc caggaaacgc ttc                               33

<210> SEQ ID NO 2
<211> LENGTH: 29
<212> TYPE: DNA
<213> ORGANISM: Artificial Sequence
<220> FEATURE:
<223> OTHER INFORMATION: synthetic mCKAP2 reverse primer

<400> SEQUENCE: 2
cacagtctga cctggcaaat catctcttg                                    29

<210> SEQ ID NO 3
<211> LENGTH: 31
<212> TYPE: DNA
<213> ORGANISM: Artificial Sequence
<220> FEATURE:
<223> OTHER INFORMATION: synthetic mCKAP2 UTR primer

<400> SEQUENCE: 3
aaaggatcca ggcgcgctca ttaagcgatg g                                 31
```

```
<210> SEQ ID NO 4
<211> LENGTH: 27
<212> TYPE: DNA
<213> ORGANISM: Artificial Sequence
<220> FEATURE:
<223> OTHER INFORMATION: synthetic lacZ reverse primer

<400> SEQUENCE: 4
gggctcgagc ggattgaccg taatgga                                          27

<210> SEQ ID NO 5
<211> LENGTH: 2304
<212> TYPE: DNA
<213> ORGANISM: Mus musculus

<400> SEQUENCE: 5
ccggcgccga ggcgcgctca ttaagcgatg gcagagtcca ggaaacgctt ccttggcagg       60
gctgcgagga atcccttgcc ggtgacccgg gacctgcagc tgcccccgac caggcgagac      120
cagccggcct tccgagaaca aagaaaacaa aaactcaagg aatatctgtt aatacgaaaa      180
acagtgtttc catacaaaca agaaaatcag atatccagag atcagaaaat gataacatct      240
gaggatcggg tccaagaagg gaaaaagtt gtgaaactca aaacagaagt ggctgataaa       300
gaaaatattg aaagtacagt tgagaaaaac tgcattccat taaaagctgg agaagtaacc      360
agctcagaaa tacataattc aaaggataat gttcaagctg tgcagttatt atctacaaga     420
gatgatttgc caggtcagac tgtgacatta gacccggcat gtcaccataa agacaataaa     480
aagatgcaaa tgactgcaga gaagcccaaa caagacagta atgtgtctaa aaagcgagtg     540
cttggctatt atcatggcca gattgttcag tctaagatta attcatttag aaagcttccc     600
agtgtcaaag gcgagagtct tacaacaacc aagaaacttc ccactactgt gtctaaagcc     660
atgaaggctc agagtgagcc tgcgaacacc gtcagcgtaa aagcctcaac tacagctgct     720
gccaccaagt ttgcagacgc taaacctgtg agcactgcgt cgaaggacac acttgtgcga     780
ccacctatcc gaagcctcca cagtagttcc cacggagctg cgaaacaggg cctcagcagg     840
ccgcttgcca atgttacagt cagaaaaggg atgcttgaca aggagtcaca tcgatcagaa     900
ccagttgtgt ccgttgtcaa agccggttct tctcaggccc catcaagaag catagcatct     960
aaagatgcag ccaggactga ttcgtctaat accagactga tggtaaagcc aaaagatact    1020
gaccagcgca gatacacgat tgcaggagca agtgttcata gatcagctca gctcaaggac    1080
accaccgcag agaggaaagc tcagatgacg gagtggagaa ctggcaaagg aaaggggcta    1140
aaacgacctc ctcattcagt agccacccag gctgagccaa agggacaaag tgaaaaccca    1200
gttgggtcct tttggactac catggcagaa gaagatgagc agagattatt tactgaaaaa    1260
gtaaacaaaa ctatttctga atgcctgaac cttattaatg agggatgccc aaaagaagaa    1320
attttggcta cattgaatga cctgattcat aatattccag atgccaaaaa acttgttaaa    1380
tattggatat gtcttgtacg tattgaacca atcacaagtc ctattgaaaa tattatctca    1440
atctatgaga aggccatcct ggcagggggct cagcctattg aagagatgcg tcatataatc    1500
atagatattc taacaacgaa gagtcaagaa aaagtcaatt tggagaaaaa tattgaggag    1560
gctcatgcaa ccaaggaacc tatccaagaa gtaaatgctg atgctaatgt agggtcagga    1620
aaaccaggag aggagaatga acatcatggc aaagttgagg tgtatgaaga tgatcaagac    1680
aacaaaataa aagatccgga tttaacaact ccggactcaa aaactgaagc aggttgcata    1740
attcgatata atgtatcttc tacacctcgg ctgcaaagta tgaaaagat gcaacatgat    1800 aaaaattcca cacttaaaga gctaaagttc ctgacaccag tgagacgctc acggcgcatt    1860
```

```
caagacaaga cttcacgact gccagccatg ttaaaagacc acgacccttc tgtgtcttcc    1920
ctggagcagt tgtctgagtt gggaggggat gcctttgtct gccgccctaa tgcagcactg    1980
tgccctctgt tctttgagac cgacgtagcg gaagaggaat aggagtcccg agtcctgagc    2040
agttatggtt gtgttactcc tgtggccctg catgtgtaca actttatcgt aggtctgaag    2100
ttgtccgcat gcctaagtat ggtacaggtg aactccacta gcttgtttgt tgtgttttta    2160
aaatataatg ttggctgctt cactttacta attacttaca gttaaagaaa caaaatcaga    2220
aaatgtagtc tatataaatt tatattttta cgttgactttt gttcctaata cgtttataat    2280
aaatatatat gtataatgtt ccaa                                           2304

<210> SEQ ID NO 6
<211> LENGTH: 9
<212> TYPE: DNA
<213> ORGANISM: Artificial Sequence
<220> FEATURE:
<223> OTHER INFORMATION: synthetic part of mCkap2 RNA

<400> SEQUENCE: 6 acgcttcct                                                              9

<210> SEQ ID NO 7
<211> LENGTH: 13
<212> TYPE: DNA
<213> ORGANISM: Artificial Sequence
<220> FEATURE:
<223> OTHER INFORMATION: synthetic part of a trans-splicing ribozyme

<400> SEQUENCE: 7
atccagggag cgt                                                        13

<210> SEQ ID NO 8
<211> LENGTH: 8
<212> TYPE: DNA
<213> ORGANISM: Artificial Sequence
<220> FEATURE:
<223> OTHER INFORMATION: synthetic part of trans-splicing ribozyme

<400> SEQUENCE: 8 gtctggat                                                               8

<210> SEQ ID NO 9
<211> LENGTH: 47
<212> TYPE: DNA
<213> ORGANISM: Artificial Sequence
<220> FEATURE:
<223> OTHER INFORMATION: synthetic part of trans-spliced transcript

<400> SEQUENCE: 9
ttaagcgatg gcagagtcca ggaaacgctt tctggattcg atggtcg                   47
```